United States Patent [19]
Schechter

[11] Patent Number: 5,880,830
[45] Date of Patent: Mar. 9, 1999

[54] SPECTRAL IMAGING METHOD FOR ON-LINE ANALYSIS OF POLYCYCLIC AROMATIC HYDROCARBONS IN AEROSOLS

[75] Inventor: Israel Schechter, Technion, Israel

[73] Assignee: Greenvision Systems Ltd., Tel Aviv, Israel

[21] Appl. No.: 790,696

[22] Filed: Jan. 29, 1997

[51] Int. Cl.[6] .................................................. G01N 21/64
[52] U.S. Cl. .................... 356/318; 250/459.1; 250/461.1
[58] Field of Search .......................... 356/318; 250/458.1, 250/461.1

[56] References Cited

U.S. PATENT DOCUMENTS

| | | |
|---|---|---|
| 3,420,634 | 1/1969 | Godsey . |
| 3,951,711 | 4/1976 | Snyder . |
| 4,031,398 | 6/1977 | Callis et al. . |
| 4,060,097 | 11/1977 | Oxford . |
| 4,855,023 | 8/1989 | Clark et al. . |
| 5,035,765 | 7/1991 | Haas . |
| 5,085,730 | 2/1992 | Cordani . |
| 5,117,466 | 5/1992 | Buican et al. . |
| 5,164,049 | 11/1992 | Clark et al. . |
| 5,257,085 | 10/1993 | Ulich et al. ................................ 356/73 |
| 5,329,353 | 7/1994 | Ichimura et al. ....................... 356/328 |
| 5,377,003 | 12/1994 | Lewis et al. ............................ 356/300 |
| 5,424,543 | 6/1995 | Dombrowski et al. ............. 356/418 X |
| 5,437,710 | 8/1995 | Grant et al. . |
| 5,469,251 | 11/1995 | Kosaka et al. ............................ 356/73 |
| 5,470,421 | 11/1995 | Nakada et al. . |
| 5,491,344 | 2/1996 | Kenny et al. ......................... 250/461.1 |
| 5,504,336 | 4/1996 | Noguchi ............................... 250/458.1 |
| 5,553,616 | 9/1996 | Ham et al. ......................... 250/339.07 |

*Primary Examiner*—Vincent P. McGraw
*Attorney, Agent, or Firm*—Mark M. Friedman

[57] ABSTRACT

A method for on-line analysis of polycyclic aromatic hydrocarbons (PAH) in aerosols. The aerosols are collected on non-fluorescing filter paper, excited to fluorescence and imaged spectrally. The images are compared with spectra in a database to determine and quantify the PAH species present. The scope of the invention is broader than fluorescence, and includes excitation analysis of particulate matter generally.

37 Claims, 5 Drawing Sheets

SPECTRAL IMAGING METHOD FOR ON-LINE ANALYSIS OF POLYCYCLIC AROMATIC HYDROCARBONS IN AEROSOLS

FIELD AND BACKGROUND OF THE INVENTION

The present invention relates to chemical analysis and, more particularly, to a method for on-line detection of polycyclic aromatic hydrocarbons (PAH) and other fluorescent contaminants in aerosols.

PAH are among the many organic materials that are commonly encountered as trace-level environmental contaminants in effluents associated with incomplete combustion, pyrolysis and other thermal degradation processes. The PAH family, defined as containing hydrocarbon species with three or more fused aromatic rings, includes many compounds suspected of being potent carcinogens. Therefore, identification and determination of emission levels of PAH is important in environmental assessment. Moreover, emission monitoring of PAH compounds is of considerable industrial importance as well, since several industrial processes can be controlled by a fast feedback of PAH composition and concentration.

Several procedures, such as gas chromatography/mass spectrometry (GC-MS), have been developed and applied for obtaining compound specific information for evaluation of PAH contamination. These procedures cannot be applied directly to particulate PAH analysis, because they all involve several sample preparation steps in which the particles are destroyed. The GC-MS methods, in particular, are complicated and expensive; they require state of the art high vacuum equipment and extensive investment of expert analyst's time. It is not cost effective to apply them routinely to samples that may not, in fact contain any relevant levels of PAH. Moreover, the GC-MS methods are not on-line methods for particulate analysis, and cannot be used for obtaining fast feedback which is required for both environmental protection and for industrial process control.

PAH compounds are produced primarily as a result of incomplete combustion of organic matter, and thus are believed to exist in both the vapor phase and the solid phase, as an integral constituent of particulate matter. Because the concentration of such pollutants in most atmospheric samples is very low, and because they are often associated with other contaminants, the identification and quantification of PAH are usually complex, time consuming and often inaccurate because of multistep isolation and determination techniques. This problem is primarily associated with analysis of PAH on aerosol particles, which is considered the most complicated task for classical methods of PAH analysis.

Nevertheless, analysis of PAH on aerosols is of intense interest to both industry and governmental environmental protection bodies. It has been proven that most PAH mass is found onto aerosol particles, rather than in the vapor phase. (This is because of the low vapor pressure of many of these compounds at ambient temperature.) The distribution of PAH as a function of aerodynamic diameter, for coke oven emission, shows that most contamination is associated with particles of diameter of 1–10 $\mu$m. The absolute concentration of PAH compounds an air is compound-dependent, and is usually in the range of 0.02–0.2 $\mu$g m$^{-3}$. Absolute concentration in the vicinity of industrial sites may be ten times higher, and concentrations in the $\mu$g m$^{-3}$ and higher, of particles having diameters between 10 and 100 $\mu$m or more, have been measured close to combustion chimneys.

Most of the currently employed analytical methods for PAH on aerosols involve (a) collection of particulate PAH by drawing a large volume of air through a filter, (b) extraction of the PAH collected on a filter paper with an organic solvent, and (c) chromatographic cleanup and separation followed by (d) identification and quantitation using one or a combination of spectroscopic and chromatographic methods, or mass spectrometry analysis in a high vacuum chamber.

There are a number of analytical difficulties associated with these traditional methods. The real-time analysis of PAH present in ambient air (fumes, coke oven emission, smoke or other gaseous media) cannot be achieved, mainly because of lack of selectivity, sensitivity, and mobility of the analytical instrumentation. Considering the above difficulties, and taking into account that traditional methods do not provide on-line and in-situ results, it follows that there is a widely recognized need for, and it would be highly advantageous to have, a method for real-time, on-line analysis of aerosol particles for PAH.

SUMMARY OF THE INVENTION

According to the present invention there is provided a method for analyzing particles for chemical components, comprising the steps of: (a) providing a database of emission spectra of the chemical components; (b) exciting said particles to emit emitted light; (c) acquiring a plurality of two dimensional images of said emitted light, each of said images being acquired at a certain wavelength, each of said images including a plurality of pixels, each of said pixels having a location in said image, each of said pixels having an intensity; (d) for a set of pixels of said images sharing a common location: comparing said intensities, as a function of said wavelength, to said emission spectra, thereby identifying the chemical components of said location.

The description below concentrates on the use of the present invention for the analysis of PAH in aerosols. Therefore, in the description below, the emission spectra are fluorescence spectra and/or phosphorescence spectra, the emitted light is fluorescence and/or phosphorescence, and the emission is excited by incident ultraviolet light. Nevertheless, it will be appreciated that the scope of the present invention includes all emission spectra that are useful in chemical analysis, including phosphorescence, Raman and infrared spectra; and that the scope of the invention includes a variety of ways of exciting the particles to emit light, including incident light in other regions of the electromagnetic spectrum, for example, visible light and infrared light, and simply heating the particles.

Preferably, the particles to be analyzed are spread out on a two-dimensional surface, so that each pixel in each two dimensional intensity image represents a part of only one particle. Generally, aerosol particles collected on the surface of a filter, as in the prior art method of PAH analysis, are spread out appropriately. When incident light is used to excite the particles, there are two general methods of acquiring the images. In the first method, the surface to be imaged is irradiated homogeneously, and the emitted light is transferred, via a suitable optical system, to a spectroscopic imaging device. Examples of such devices are the acousto-optic tunable filter and the scanning interferometer described by Lewis et al. in U.S. Pat. No. 5,377,003, which is incorporated by reference for all purposes as if fully set forth herein; the scanning interferometer described by Cabib et al. In U.S. Pat. No. 5,539,517 and produced by Applied Spectral Imaging, Ltd. Of Migdal Haemek, Israel, under the name "ASI SD2000", and the liquid crystal tunable filter described in Fluorescence Imaging Spectroscopy and Microscopy (Xue Feng Wang & Brian Herman, editors, John Wiley & Sons, Inc., 1996). In the second method, the surface to be imaged is scanned using a focused beam of light, and the emitted light is analyzed by a conventional spectrometer. Under both methods, the spectrally decomposed emitted light is imaged by one of several methods. The straightforward method uses a solid-state area image sensor array such as an array of charge coupled detectors (CCD), with each detector of the array acquiring one pixel of each image. Another method is to acquire each image one row of pixels at a time using a scanning diode array. CCD arrays recently have become available that are sufficiently dense that several images corresponding to several different wavelengths can be acquired simultaneously. For example, a 4096×4096 CCD array can acquire 64 512×512 images simultaneously, at 64 different wavelengths. As an alternative to the spectrometers, these large CCD arrays can be used with a large number (64 in the example given) of narrow band optical filters to obtain single-wavelength images. Under this alternative, the sample must be moved, for example on a piezoelectric stage, from one filter to another. In the analysis of aerosol particles for PAH, the optical system includes a microscope, so that the final single-wavelength images are sufficiently magnified to resolve the target particles at the desired resolution of one or more pixels per particle.

The acquired images are digitized and analyzed by standard methods. Preferably, one of the steps in the analysis is the blanking of pixels whose intensity is less than a predetermined threshold. The resulting images then are images of the particles themselves, or, in the case of PAH analysis of aerosol particles by fluorescence, images of the portion of the surface of the particles that is occupied by PAH species.

Given a set of pixels, from the same location in several images acquired at several wavelengths, there are well established methods for comparing the intensities of these pixels to the emission spectra in the database to determine the chemical composition of the emission sources. In particular, there are several chemometric methods that have been used successfully in connection with liquid phase fluorescence. The most powerful of these is multivariate analysis in general, and principal component regression (PCR) or least squares analysis (for example, partial least squares analysis (PLS) or non-linear least squares fitting) in particular. See, for example, H. Martens and T. Naes, Multivariance Calibration (John Wiley & Sons, 1989). Another method that has been applied successfully to analyzing liquid phase fluorescence is fuzzy logic analysis. See, for example, J. C. Bezdek and S. K. Pal (eds.), Models for Pattern Recognition, IEEE Press, 1992, and R. R. Yager and L. A. Zadeh (eds.), An Introduction to Fuzzy Logic Applications in Intelligent Systems, Kluwer Academic Publications, 1992. Preferably, both multivariate regression and fuzzy logic analysis are used, to exploit the redundancy inherent in using two independent methods. These methods are based on the spectra of pure compounds and of mixtures that are likely to occur in particular scenarios, either in crystalline form or adsorbed on solid particles, and account for the detailed structure of the superimposed spectra from mixtures, including crystals of mixed composition. In cases where this resolution is inadequate, time-resolved fluorescence methods are applied. See, for example, Anita Cardamone et al., Simple Time Resolved Fluorescence Based on Nanosecond Digital Oscilloscope and Diode Pumped Solid State Laser, Applied Spectroscopy vol. 97 pp. 207–210 (1993), Rande W. St. Germain et al., Inside Tunable Laser Fluorescence Analysis of Hydrocarbons, SPIE vol. 1637 pp. 151–162 (1992), and Kenneth Ghiggino et al., Resolution of Heterogeneous Fluorescence By the Combined Use of Indirect Excitation Decay Associated Spectral Analysis and Principle Factor Analysis, Chem. Soc. Faraday Trans. vol. 86 pp. 3853–3860 (1990). In these methods, the images are acquired as functions both of wavelength and of time. The resolution in this case is based on the fact that each fluorescing compound has its own characteristic decay time subsequent to excitation by a pulse of ultraviolet light.

Two important advantages of the present invention for PAH analysis, over the wet chemistry of the prior art, are that the PAH are not diluted and mixed by the solvent used for extraction, and that, under condensation conditions, PAH tends to be deposited on aerosol particles in the form of crystals, or in an enriched solid solution in the body of the aerosol particle itself (D. F. Eggers, N. W. Gregory, G. D. Haliey and B. S. Rabinovich, Physical Chemistry, Wiley, New York, 1964). Thus, the present invention has inherently higher mixture resolution and sensitivity than the prior art methods. The nature and spatial distribution of PAH species associated with pollution aerosols can be diagnostic of the source of the pollution. If a particular source is of interest, the fluorescence spectra to which the images are compared are restricted to the spectra of the species likely to be emitted by the source. For example, motor vehicles tend to emit predominantly dibenz(a,I)anthracene, picene and coronene; whereas stationary sources such as power plants tend to emit coronene in addition to the three PAHs emitted by motor vehicles.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is of a method of particulate chemical analysis which can be automated for real-time on-line analysis of aerosols. Specifically, the present invention can be used to analyze aerosols for PAH.

The principles and operation of particulate analysis according to the present invention may be better understood with reference to the drawings and the accompanying description.

Figure 1:
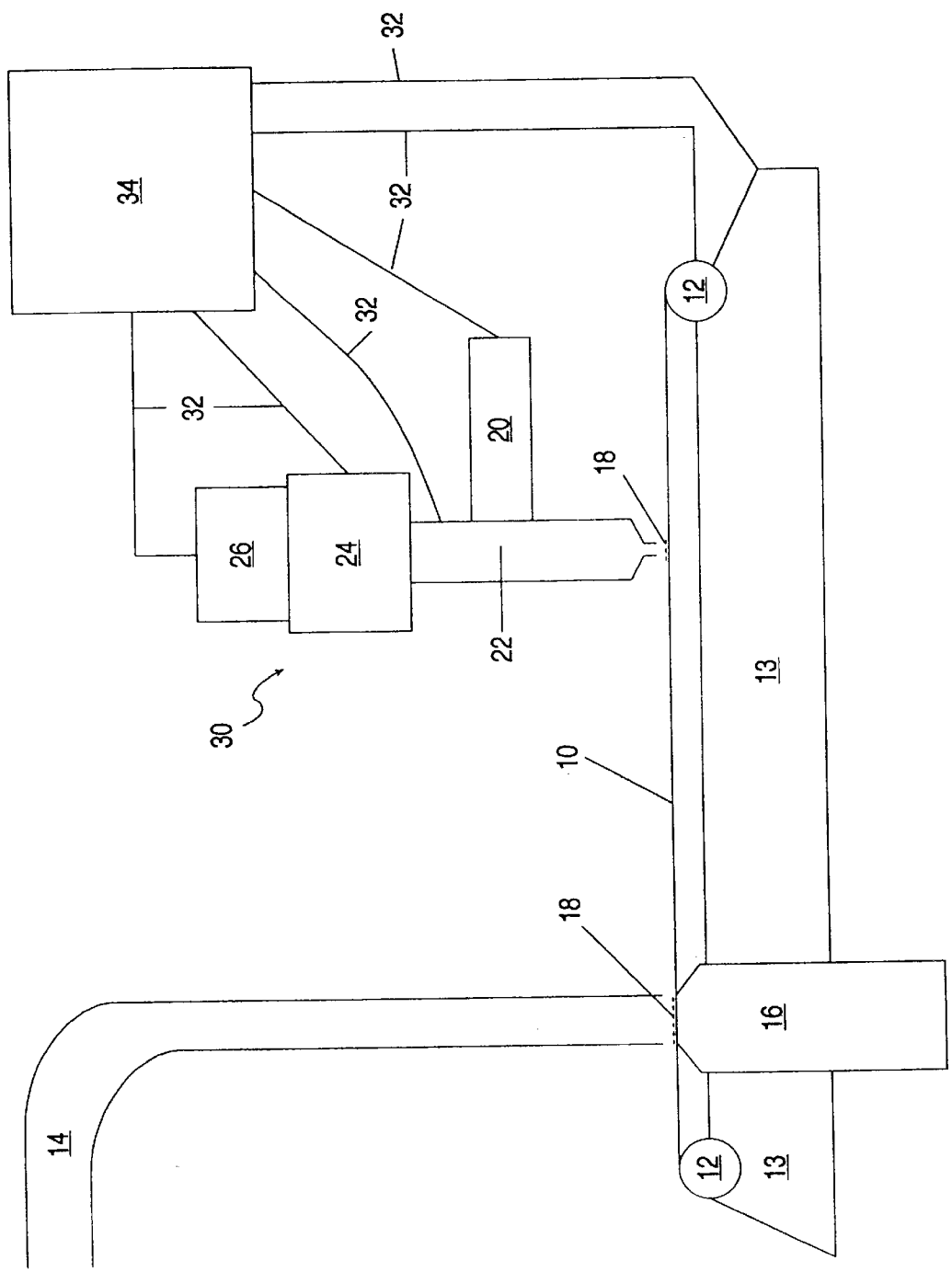
FIG. 1 is a schematic diagram of a system for monitoring PAH in aerosols.

Referring now to the drawings, FIG. 1 is a schematic diagram of an automatic on-line real-time system for monitoring PAH in aerosols. A roll of a non-fluorescing substrate 10 such as non-fluorescing filter paper is mounted on a pair of rollers 12, which move substrate 10 from left to right as seen in FIG. 1. A high volume air pump 16 sucks in contaminated air via a pipe 14 and through substrate 10, depositing aerosol particles 18 on substrate 10. Optionally, a filtration system (not shown), such as a 10PM high volume particle sampler, may be placed in pipe 14 to select particles below a certain size, for example, 10μ. Rollers 12 move aerosol particles 18 to a position for viewing under a spectroscopic imaging system 30 that includes a source of ultraviolet light 20, an optical system 22, a spectroscopic imaging device 24 and a CCD camera 26 having a suitable sensitivity and dynamic range. Typical spectroscopic imaging systems are described, for example, in the Lewis et al. patent cited above, and will not be elaborated further herein.

Components 20, 22, 24 and 26 of spectroscopic imaging system 30 are connected by suitable control/data links 32 to a control system 34. Light source 20 illuminates particles 18 homogeneously via optical system 22, as shown in FIGS. 6 and 8 of the Lewis et al. patent cited above. In other embodiments of the present invention, light source 22 directs ultraviolet light directly onto particles 18, without the intervention of optical system 22. Rollers 12 also are connected by a control/data link 32 to control system 34 so that substrate 10 can be advanced under the control of control system 34. Rollers 12 are mounted on a stage 13 which has two degrees of freedom of motion: laterally (into and out of the plane of FIG. 1) and vertically. The vertical motion of stage 13 is used to effect autofocusing. Stage 13 also is controlled by control system 34 via a control/data link 32. The combined motions of rollers 12 and stage 13 allow substrate 10 to be moved laterally in three directions under optical system 22.

The preferred spectroscopic imaging device 24 is a scanning interferometer. The image acquired via an acousto-optic tunable filter tends to drift laterally over time. This can be overcome during image processing, however. A symbol such as a cross is placed on the background against which particles 18 are imaged, and the images are aligned by shifting them so that the symbol is in the same position on all images.

Control system 34 is based on a personal computer, and includes a frame grabber, for acquiring images from camera 26, as well as other hardware interface boards for controlling rollers 12, stage 13 and the other components 20, 22 and 24 of spectroscopic imaging system 30. The software of control system 34 includes a database of PAH fluorescence spectra and code for implementing the image processing and classification algorithms described below.

Preferably, rollers 12 are used to move substrate 10 to the right, as seen in FIG. 1, in a stepwise fashion, so that while control system 34 is acquiring and analyzing images of one sample of particles 18, pump 16 is collecting the next sample of particles 18. Rollers 12 and stage 13 also are used to move particles 18 a much shorter distance laterally under optical system 22, to allow control system 34 to acquire images from several fields of view in a sample.

Figure 2:
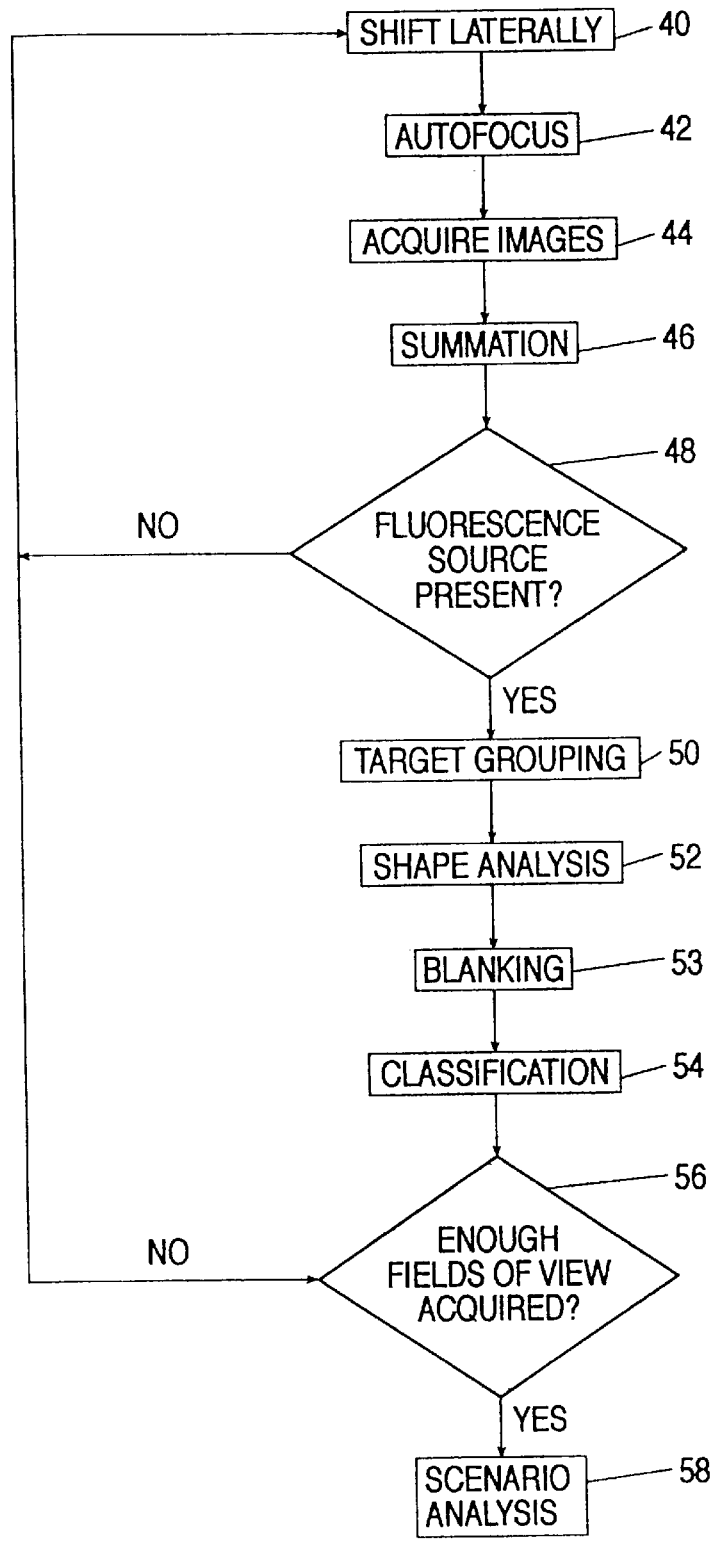
FIG. 2 is an overall flow diagram of the detection and classification of PAH.

FIG. 2 is an overall flow diagram of the process of automatic detection and classification of PAH. The first step is to find a field of view that contains particles 18 of interest. This is done by shifting the field of view laterally (block 40), using rollers 12 and stage 13; autofocusing (block 42); acquiring a set of images at the desired wavelengths (block 44); summing the single-wavelength images to give a summed, or gray level, image (block 46); and checking the summed image for pixels whose intensities exceed a preset threshold related to background intensity. Note that there is a one to one correspondence between the pixels of the summed image and what is referred to herein as the "common locations" of pixels of the single-wavelength images. The criterion for a fluorescing particle being present in the field of view (block 48) is that the fraction of pixels of the summed image whose intensities exceed the threshold be sufficiently high. If the criterion is not satisfied, another field of view is selected. Preferably, this is done by shifting the field of view (block 40) randomly, because it is not known in advance where the particles of interest are. Adjacent non-zero pixels of the summed image are grouped into targets suspected to represent PAH-bearing aerosol particles (block 50). Optionally, the shapes of the targets are determined (block 52) so that targets not shaped like PAH-bearing aerosols may be culled during the classification process. Pixels of single-wavelength images that correspond to below-threshold pixels in the summed image are blanked (block 53). Finally the target spectra are classified: in each target, the pixel intensities are compared, location by location, to the fluorescence spectra in the database to assay the PAH species present in the target (block 54).

Figure 3:
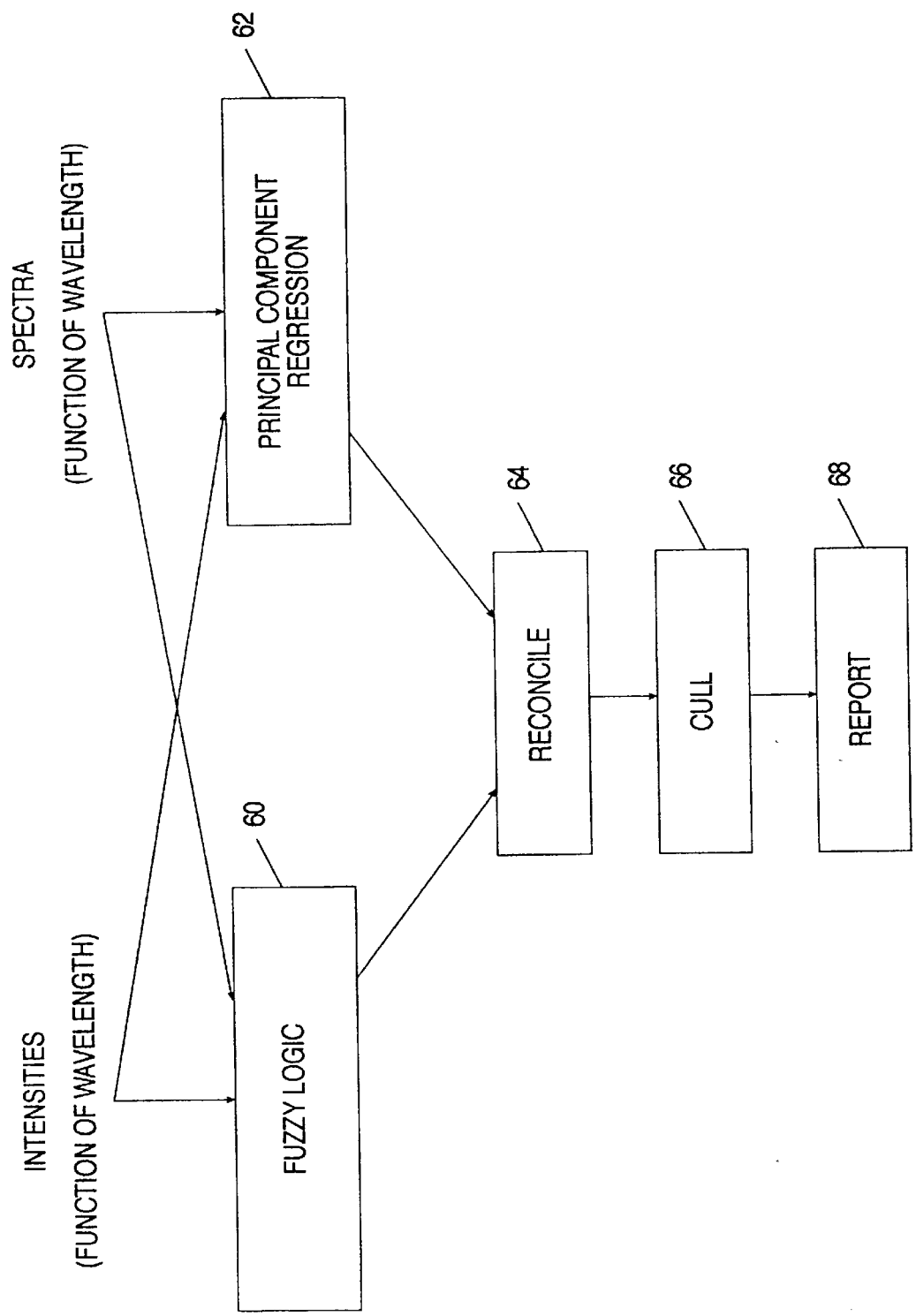
FIG. 3 is a flow diagram of the classification process.

FIG. 3 is a flow diagram of the classification process used in the assay. Essentially, the classification process is a matter of looking for a linear combination of the spectra that matches the intensities. The coefficients of the linear combination then are proportional to the amounts of the various PAH species at the location sampled. The linear combination is determined by two methods, fuzzy logic analysis (block 60) and principal component regression (block 62). Both of these methods yield both estimates of PAH species abundances and uncertainty measures for those estimates. The two sets of estimates are reconciled (block 64) to give a final set of estimated abundances.

Figure 4:
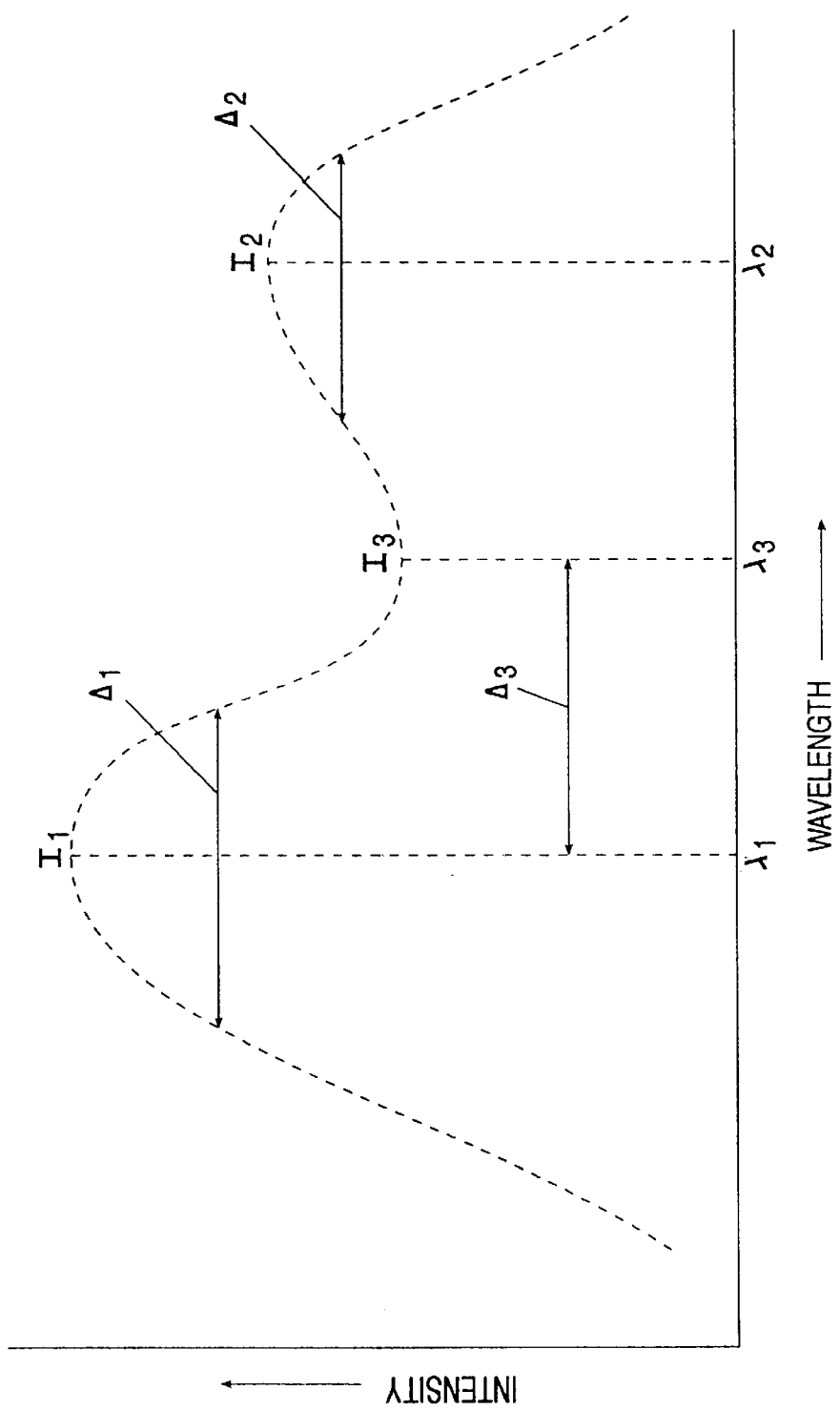
FIG. 4 is a generalized intensity curve for illustrating fuzzy logic description parameters.

FIG. 4 is a generalized intensity curve (intensity I as a function of wavelength $\lambda$), illustrating five of the description parameters used in the fuzzy logic analysis. This curve has two peaks, one with a peak intensity $I_1$ at wavelength $\lambda_1$ and the other with a peak intensity $I_2$ at wavelength $\lambda_2$. The minimum intensity between the two peaks is $I_3$, at a wavelength $\lambda_3$. The full width at half amplitude of the first peak is designated by $\Delta_1$. The full width at half amplitude of the second peak is designated by $\Delta_2$. The difference between $\lambda_1$ and $\lambda_3$ is $\Delta_3$. The five description parameters illustrated in FIG. 4 are:

peak height ratio $I_1/I_2$ peak full width at half amplitude ratio $\Delta_1/\Delta_2$ number of peaks peak to minimum ratio $\Delta_1/\Delta_3$ peak wavelength ratio $\lambda_1/\lambda_2$ PAH species abundances having been obtained at each location in each target, the locations and targets are analyzed for consistency with a PAH emissions model (FIG. 3, block 66), using two criteria:

1. Because PAH tends to be deposited on aerosol particles in the form of pure single crystals, neighboring locations are expected to have similar compositions. Therefore, the next step in the overall detection and classification process is the grouping of neighboring locations into neighborhoods of common composition, using well-known regression techniques. This step also serves as a noise filter: it is unlikely that a pixel (i,j) will have a different composition than a neighboring pixel (k,l), where $i-1 \leq k \leq i+1$ and $j-1 \leq l \leq j+1$ (neighborhood decision concept).

2. (Optional) If target shapes have been determined (FIG. 2, block 52), and information is available about expected particle shapes and sizes, then targets whose shapes and sizes are outside the expected range are discarded. For example, it may be known a priori that a particular emission source does not emit needle-like aerosol particles. In that case, targets whose aspect ratio exceeds a threshold are discarded.

Figure 5:
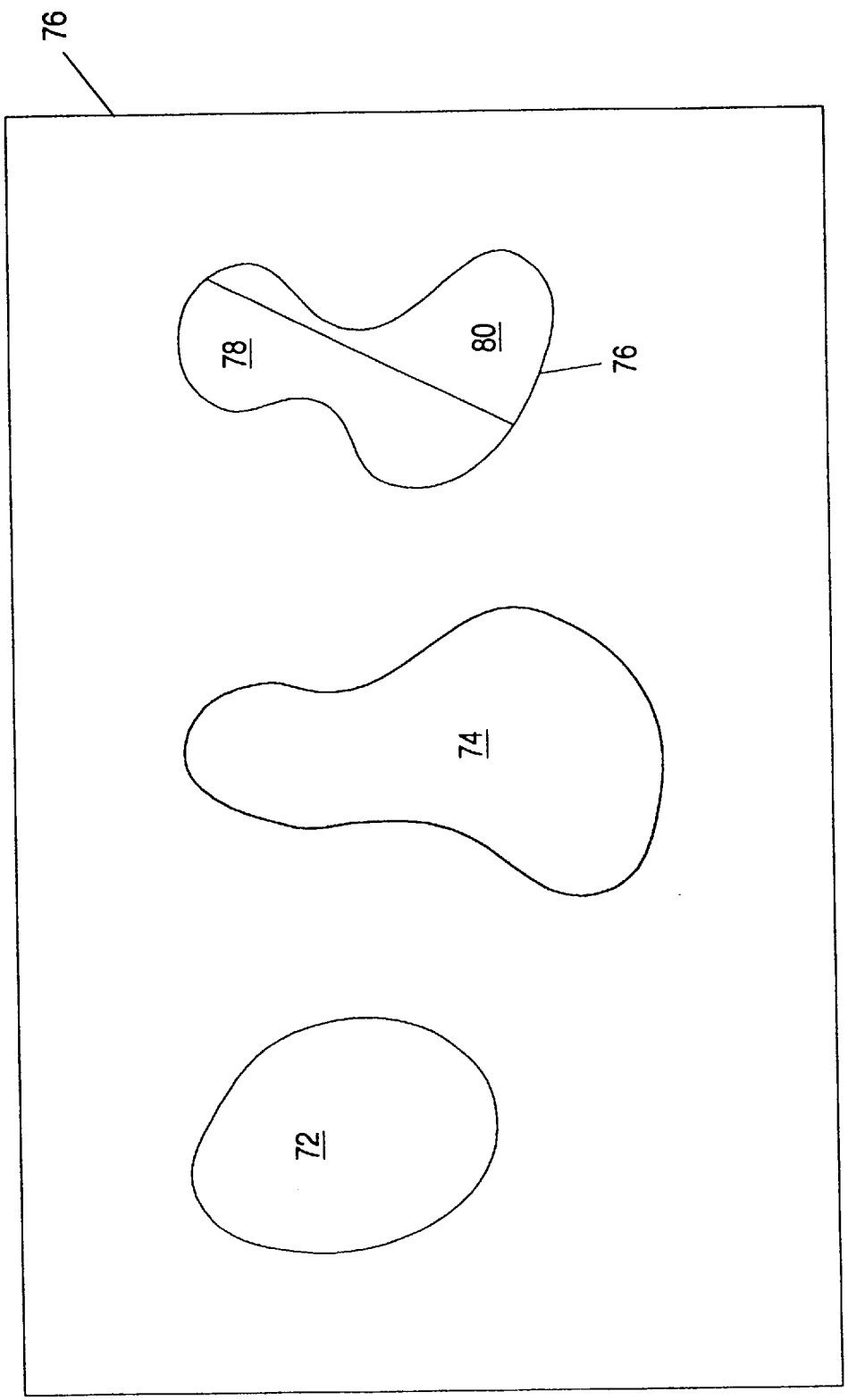
FIG. 5 is a schematic illustration of a final processed image.

Locations and targets not satisfying the criteria are culled (block 66). The surviving targets are assumed to be images of PAH-bearing aerosols. The results of the analysis now are reported to the user (block 68), for example in the form of a processed image. FIG. 5 is a schematic illustration of a final processed image 70 of three particles 72, 74 and 76. Particle 72 has been classified as containing a first PAH species. Particle 74 has been classified as containing a second PAH species. Particle 76 has been classified as containing two PAH species in two neighborhoods 78 and 80.

When PAH detection and classification has been performed on a large enough number of fields of view (FIG. 2 block 56), the raw data are analyzed by a scenario analysis algorithm (FIG. 2 block 58) to convert them to estimates of absolute PAH concentrations. Typically, aerosols are collected and analyzed in this manner at several related sites and at several times each day, for each source type or plant process being monitored.

While the invention has been described with respect to a limited number of embodiments, it will be appreciated that many variations, modifications and other applications of the invention may be made.

What is claimed is:

1. A method for analyzing particles for chemical components, comprising the steps of:
   (a) providing a database of emission spectra of the chemical components;
   (b) exciting the particles to emit emitted light;
   (c) acquiring a plurality of two dimensional images of said emitted light, each of said images being acquired at a certain wavelength, each of said images including a plurality of pixels, each of said pixels having a location in said image, each of said pixels having an intensity; and
   (d) for a set of pixels of said images sharing a common location: comparing said intensities, as a function of said wavelength, to said emission spectra, using both multivariate analysis and fuzzy logic analysis based on at least one description parameter, thereby identifying the chemical components of said location.

2. The method of claim 1, wherein said exciting is effected by directing excitation light at said particles.

3. The method of claim 2, wherein said excitation light is visible light.

4. The method of claim 2, wherein said excitation light is ultraviolet light.

5. The method of claim 2, wherein said excitation light is infrared light.

6. The method of claim 2, wherein said excitation light is directed homogeneously at said particles.

7. The method of claim 6, wherein said acquiring of said images is effected using a scanning interferometer.

8. The method of claim 6, wherein said acquiring of said images is effected using a liquid crystal tunable filter.

9. The method of claim 6, wherein said acquiring of said images is effected using an acousto-optic tunable filter.

10. The method of claim 2, wherein said directing of said excitation light at said particles is effected by scanning a laser beam across said particles.

11. The method of claim 10, wherein said acquiring of said images is effected using a spectrometer.

12. The method of claim 1, wherein said comparing of said intensities to said emission spectra is effected only for pixels whose intensity exceeds a threshold.

13. The method of claim 1, wherein said multivariate analysis includes principal component regression.

14. The method of claim 1, wherein said multivariate analysis includes least squares analysis.

15. The method of claim 1, wherein said at least one description parameter includes at least one description parameter selected from the set consisting of peak height ratio, peak full width at half amplitude ratio, number of peaks, peak to minimum ratio and peak wavelength ratio.

16. The method of claim 1, further comprising the step of:
   (e) grouping neighboring said common locations having similar said identified chemical components, thereby forming a target.

17. The method of claim 16, further comprising the step of:
   (f) culling said targets.

18. The method of claim 1, further comprising the step of:
   (e) culling said common locations.

19. The method of claim 1, wherein said plurality of images is acquired at a plurality of aquisition times, the method further comprising the steps of:
   (e) providing a database of emission decay times of the chemical components;
   (f) for a set of pixels of said images sharing a common location: comparing said intensities, as a function of said acquisition times, to said emission decay times, thereby identifying the chemical components of said location.

20. The method of claim 1, further comprising the step of:
   (e) reconciling said identification based on said multivariate analysis with said identification based on said fuzzy logic analysis.

21. The method of claim 16, wherein said target has a certain shape, the method further comprising the step of:
   (f) comparing said shape of said target to an expected shape of particles of said similar identified chemical components.

22. A method for analyzing aerosol particles for PAH, comprising the steps of:
   (a) providing a database of emission spectra of the PAH;
   (b) collecting the particles on a surface;
   (c) exciting said collected particles on said surface to emit emitted light;
   (d) acquiring a plurality of two dimensional images of said emitted light, each of said images being acquired at a certain wavelength, each of said images including a plurality of pixels, each of said pixels having a location in said image, each of said pixels having an intensity; and
   (e) for a set of pixels of said images sharing a common location: comparing said intensities, as a function of said wavelength, to said emission spectra, thereby identifying the PAH at said location.

23. The method of claim 22, wherein said comparing of said intensities to said emission spectra includes both multivariate analysis and fuzzy logic analysis.

24. The method of claim 23, further comprising the step of:
   (f) reconciling said identification based on said multivariate analysis with said identification based on said fuzzy logic analysis.

25. The method of claim 23, further comprising the step of:
   (f) grouping neighboring said common locations having similar said identified PAH, thereby forming a target.

26. The method of claim 25, wherein said target has a certain shape, the method further comprising the step of:

(g) comparing said shape of said target to an expected shape of particles of said similar identified PAH.

27. The method of claim 22, wherein said comparing of said intensities to said emission spectra includes both multivariate analysis and fuzzy logic analysis.

28. The method of claim 23, further comprising the step of:
(f) reconciling said identification based on said multivariate analysis with said identification based on said fuzzy logic analysis.

29. The method of claim 23, further comprising the step of:
(f) grouping neighboring said common locations having similar said identified chemical components, thereby forming a target.

30. The method of claim 25, wherein said target has a certain shape, the method further comprising the step of:
(g) comparing said shape of said target to an expected shape of particles of said similar identified chemical components.

31. A method for analyzing particles for chemical components, comprising the steps of:
(a) providing a database of emission spectra of the chemical components;
(b) exciting said particles to emit emitted light;
(c) acquiring a plurality of two dimensional images of said emitted light, each of said images being acquired at a certain wavelength, each of said images including a plurality of pixels, each of said pixels having a location in said image, each of said pixels having an intensity;
(d) identifying said locations corresponding to the chemical components; and
(e) only for said locations corresponding to the chemical components: for a set of pixels of said images sharing a common location: comparing said intensities, as a function of said wavelength, to said emission spectra, thereby identifying the chemical components of said location.

32. The method of claim 31, further comprising the step of:
(f) grouping neighboring said locations having similar said identified chemical components, thereby forming a target.

33. The method of claim 32, wherein said target has a certain shape, the method further comprising the step of:
(g) comparing said shape of said target to an expected shape of particles of said similar identified chemical components.

34. A method for monitoring chemical species discharged as particles from a source, comprising the steps of:
(a) providing a database of emission spectra of the chemical species and of associated particle morphologies;
(b) exciting said particles to emit emitted light;
(c) acquiring a plurality of two dimensional images of said emitted light, each of said images being acquired at a certain wavelength, each of said images including a plurality of pixels, each of said pixels having a location in said image, each of said pixels having an intensity;
(d) for a set of pixels of said images sharing a common location: comparing said intensities, as a function of said wavelength, to said emission spectra, thereby identifying the chemical species of said location;
(e) grouping neighboring said locations having similar said identified chemical species, thereby forming a target having a certain morphology; and
(f) comparing said morphology of said target to said particle associated with said identified chemical species.

35. The method of claim 34, wherein said particle morphologies include characteristics selected from the list consisting of particle shape and particle size, and wherein said target morphology includes characteristics selected from the list consisting of target shape and target size.

36. The method of claim 34, wherein said database includes said emission spectra and said morphologies only for the chemical species monitored.

37. A method for analyzing microscopic particles for chemical components, comprising the steps of:
(a) providing a database of emission spectra of the chemical components;
(b) collecting the particles on a surface;
(c) exciting said collected particles on said surface to emit emitted light;
(d) acquiring a plurality of two dimensional images of said emitted light, each of said images being acquired at a certain wavelength, each of said images including a plurality of pixels, each of said pixels having a location in said image, each of said pixels having an intensity; and
(e) for a set of pixels of said images sharing a common location: comparing said intensities, as a function of said wavelength, to said emission spectra, thereby identifying the chemical components at said location.

\* \* \* \* \*